United States Patent [19]

Lemay

[11] Patent Number: 5,013,292

[45] Date of Patent: May 7, 1991

[54] SURGICAL CORRECTION OF FEMALE URINARY STRESS INCONTINENCE AND KIT THEREFOR

[75] Inventor: Claude Lemay, Ste. Croix, Canada

[73] Assignee: R. Laborie Medical Corporation, Quebec, Canada

[21] Appl. No.: 315,279

[22] Filed: Feb. 24, 1989

[51] Int. Cl.$^5$ .......................................... A61B 19/00
[52] U.S. Cl. .............................. 600/30; 128/DIG. 25; 606/232
[58] Field of Search ............... 128/830, 831, 834, 839, 128/840, DIG. 25; 600/29, 30; 606/144, 148, 216, 222, 228-233

[56] References Cited

U.S. PATENT DOCUMENTS

| | | | |
|---|---|---|---|
| 3,066,667 | 12/1962 | Berry | 128/DIG. 25 |
| 3,372,695 | 3/1968 | Beliveau et al. | 128/DIG. 25 |
| 3,675,639 | 7/1972 | Cimber | 128/840 |
| 3,789,828 | 2/1974 | Schulte | 600/30 |
| 4,172,458 | 10/1979 | Pereyra | 606/144 |
| 4,493,323 | 1/1985 | Albright et al. | 606/144 |
| 4,738,255 | 4/1988 | Goble et al. | 606/232 |
| 4,741,330 | 5/1988 | Hayhurst | 606/232 |
| 4,823,794 | 4/1989 | Pierce | 606/232 |
| 4,857,041 | 8/1989 | Annis et al. | 600/30 |

FOREIGN PATENT DOCUMENTS 285164 10/1970 U.S.S.R. ................................. 600/29

OTHER PUBLICATIONS

Marshall et al., *Surg. Gyn. Obst.*, 1949, pp. 509-518.
Pereyra, *West. J. Surg., Obst. & Gynec.*, 1959, pp. 223-226.
Burch, *Am. J. Obst. & Gynec.*, 2/1961, pp. 281-290.
Stamey et al., *Surg. Gyn. & Obst.*, 3/1975, 140:355-360.
Stamey, *Surg. Gyn. & Obst.*, 4/1973, 136: 547-554.
Pereyra et al., *Obst. Gyn.*, 10/1967, vol. 30, No. 4, pp. 557-546.

*Primary Examiner*—Stephen C. Pellegrino
*Assistant Examiner*—Ralph A. Lewis
*Attorney, Agent, or Firm*—Sherman and Shalloway

[57] ABSTRACT

A surgical kit is provided, for a urethropexy procedure, comprising at least one needle (comprising a cannula and a trocar), a pair of implants and a tray for supporting and packaging the needle(s) and implants. The kit is sterilizable. A procedure for urethropexy is disclosed which may be carried out under local anesthesia.

21 Claims, 11 Drawing Sheets

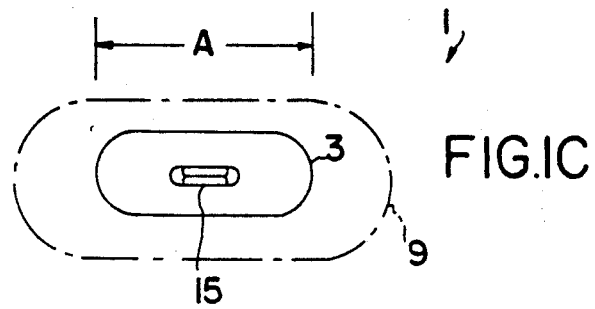
FIG.IC
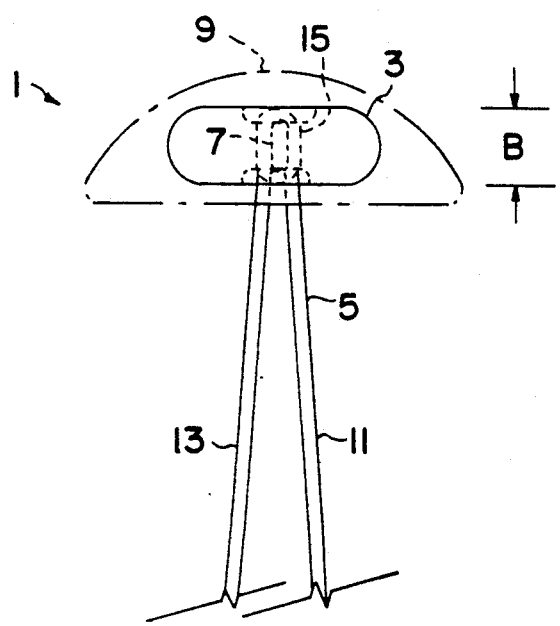
FIG.IA
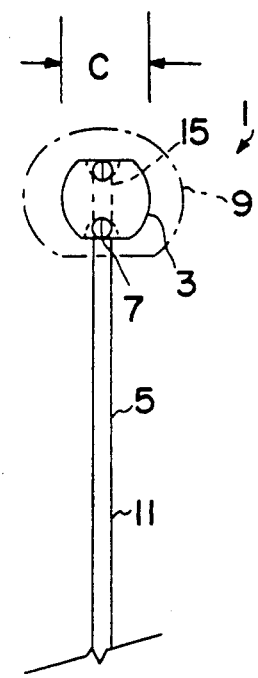
FIG.IB

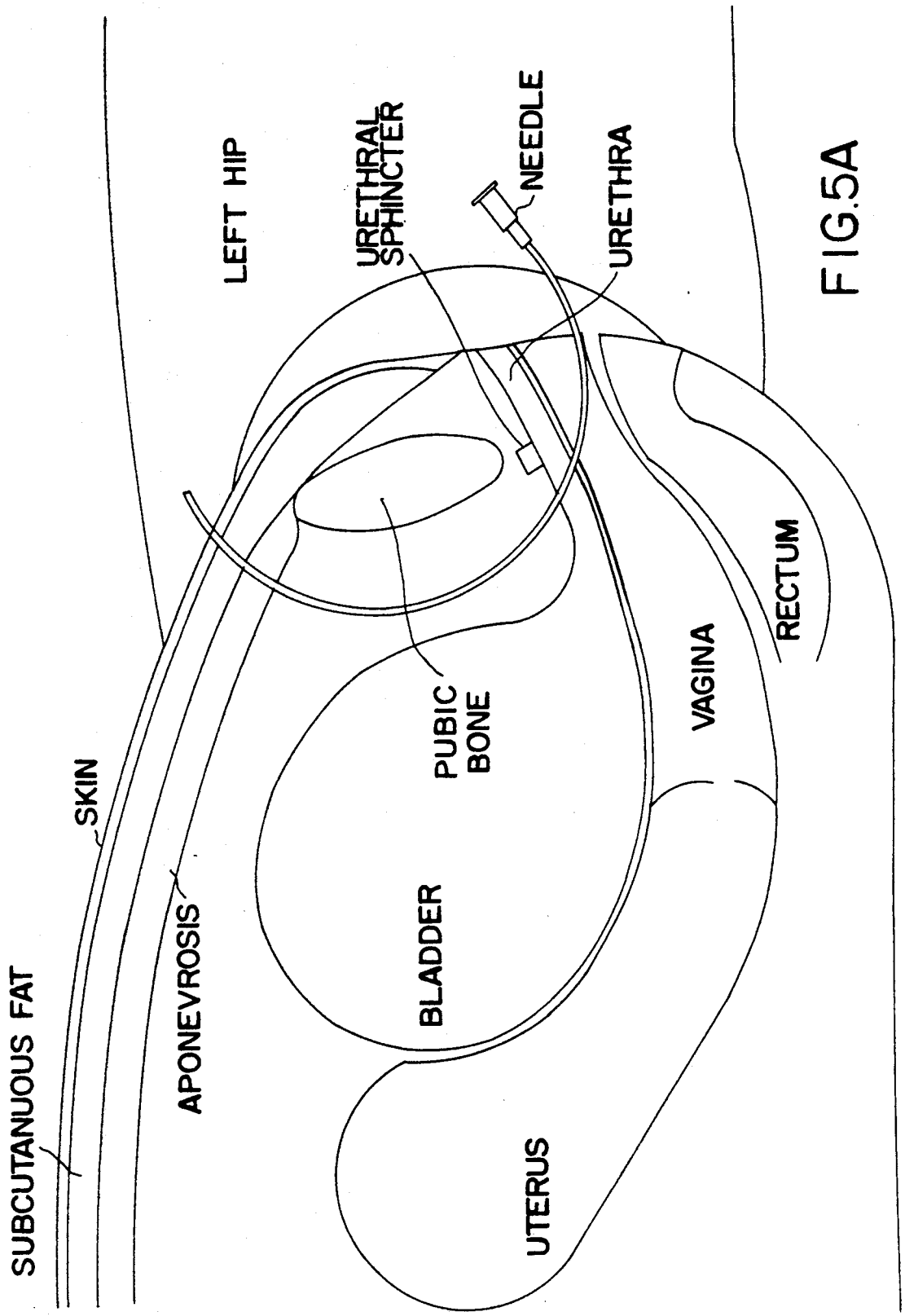

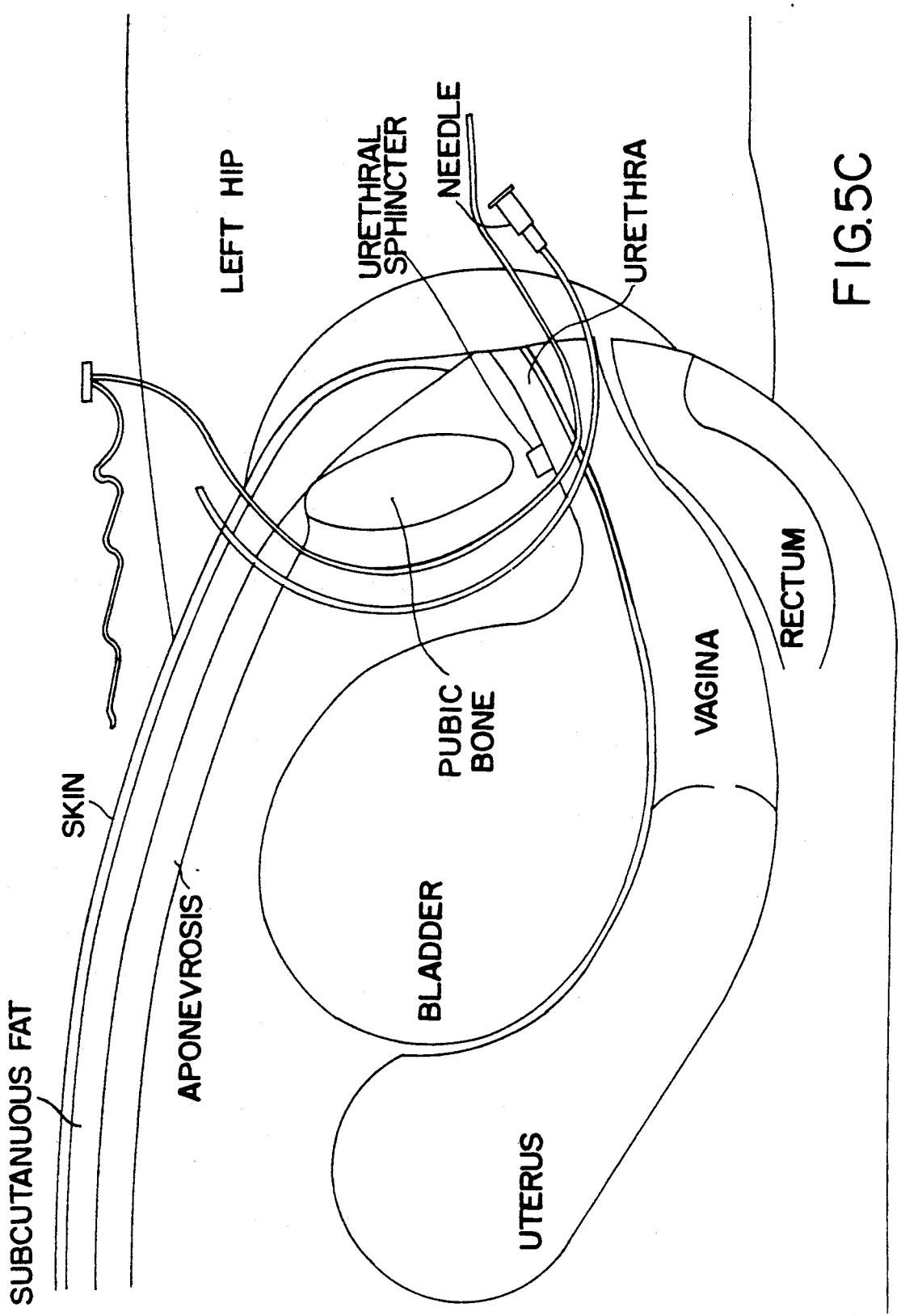

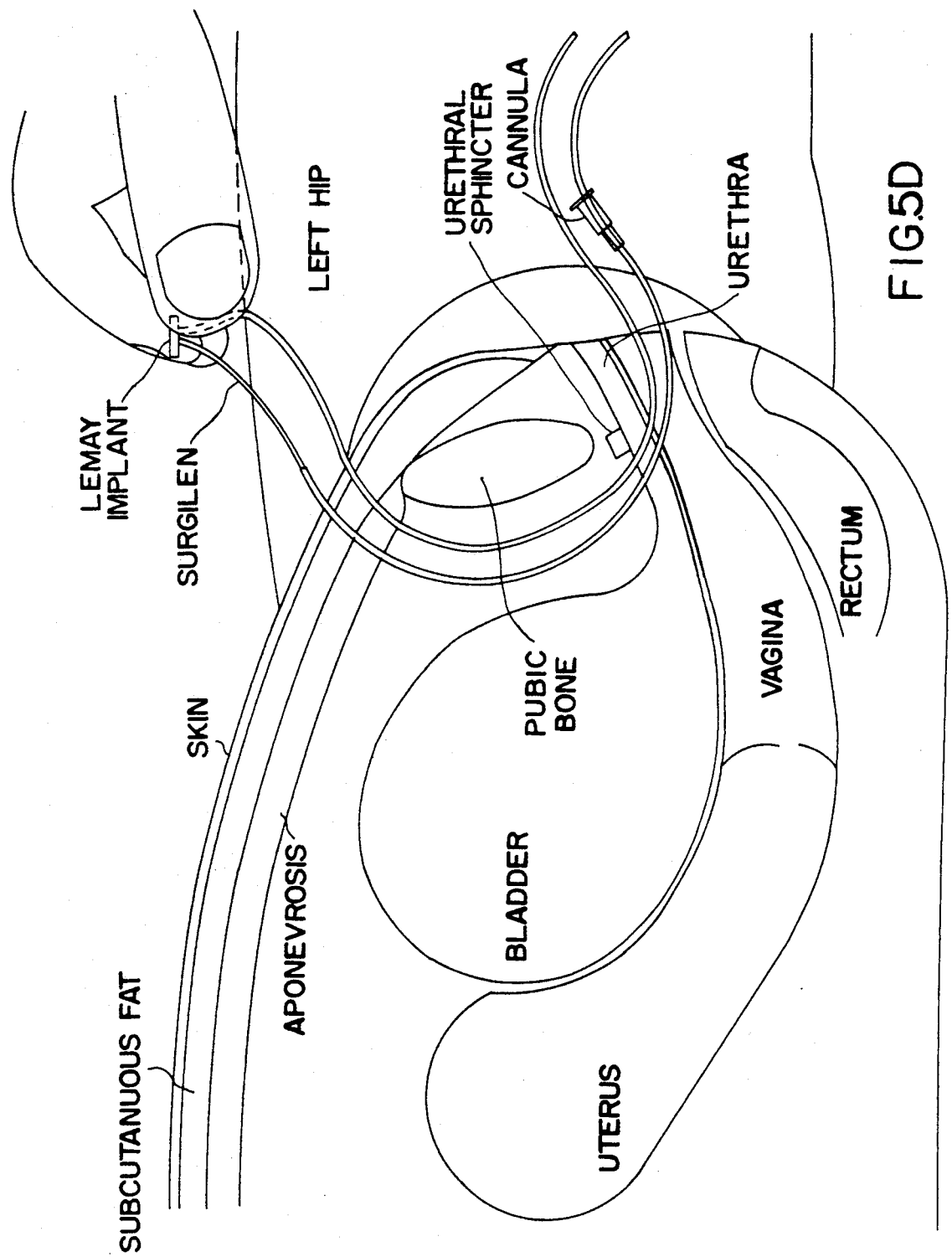

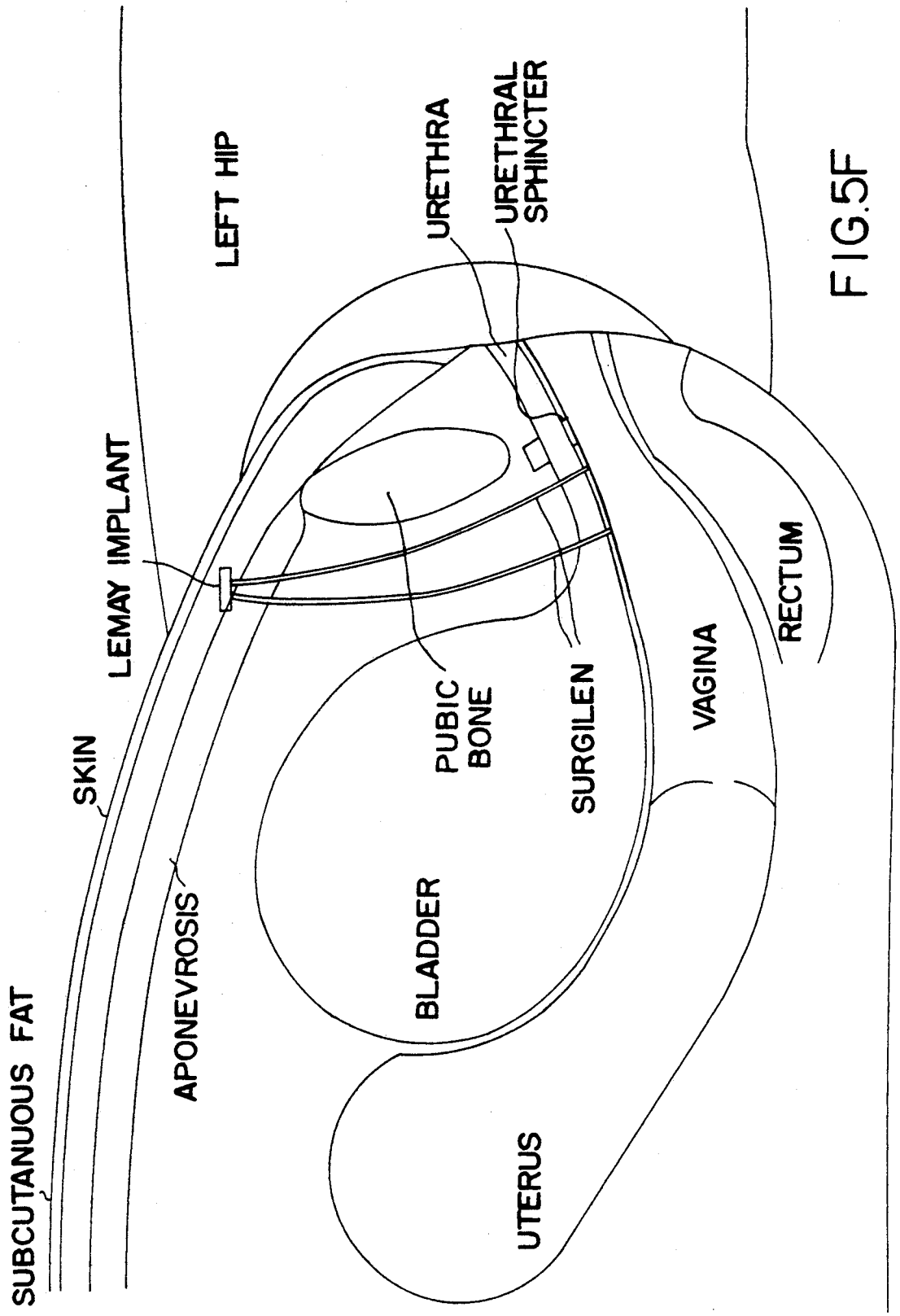

SURGICAL CORRECTION OF FEMALE URINARY STRESS INCONTINENCE AND KIT THEREFOR

BACKGROUND OF THE INVENTION

1. Field of the Invention

The present invention is directed to a method for the surgical correction of female urinary stress incontinence and a kit therefor. More particularly, the present invention is directed to a surgical technique for urethropexy and a kit containing materials to effectuate the technique.

2. Description of the Prior Art

Female urinary stress incontinence is treated urgically by tying the urethro-vesical junction to the back of the symphysis pubis. Kelly 1913, Marshall 1949, Pereyra 1959, Burch 1961, Stamey 1973, Stamey 1975, Cobb et al. 1978 and Pereyra et al. 1967 have all helped to refine the technique and to improve the results. However, these prior techniques have required the utilization of general anesthesia and have not been conducive to repeat performances, even though such re-operation may be dictated in numerous cases.

SUMMARY OF THE INVENTION

It is an object of the invention to provide a surgical technique for urethropexy which may be performed under local anesthesia.

It is a further object of the invention to provide a surgical technique for urethropexy which is generally applicable to patients in need thereof, allows for repetition thereof, if necessary, while reducing morbidity and cost.

It is a still further object of the invention to provide a kit containing devices necessary to effectuate the surgical technique.

It is a yet further object to provide a device to effect said urethropexy, when necessary.

These and other objects of the invention, as will become apparent hereinafter, have been attained by the provision of a method for surgically correcting female urinary stress incontinence comprising the steps of:

(1) providing a pair of implants, each of said implants comprising a head portion and a suture portion, said head portion adapted to rest on the symphysis pubis, said suture portion comprising a surgical suture acceptable, substantially non-biodegradable thread connected to said head portion, said thread having a first end and a second end disposed on a single side of said head portion;

(2) providing at least one needle, said at least one needle comprising a cannula and a trocar, said cannula being receivable of said trocar, said trocar being removably disposable within said cannula, said at least one needle being bendable to a desired degree of curvature, said first and second ends of said thread being guidingly receivable within said cannula;

(3) incising only the vaginal mucosa with an incision about 1 cm in length at the urethro-vesical junction;

(4) introducing said needle at the right distal extremity of said vaginal incision and non-traumatizingly guiding said needle along the symphysis pubis to a first point about 3 cm to the right of a median line at the superior border of the symphysis pubis and passing said needle through the skin at this first point;

(5) incising the skin with a cutaneous incision about 0.5 cm in length at said first point;

(6) removing said trocar from said needle while leaving the cannula in place;

(7) introducing the first end of said thread from one of said pair of implants into said cannula until it protrudes into the vagina;

(8) withdrawing said cannula through the vagina;

(9) introducing said needle at the right distal extremity of said vaginal incision and non-traumatizingly guiding said needle along the symphysis pubis to said incision of step (5);

(10) removing said trocar from said needle while leaving the cannula in place;

(11) introducing the second end of said thread from said one of said pair of implants into said cannula until it protrudes into the vagina;

(12) withdrawing said cannula through the vagina;

(13) introducing said needle at the left distal extremity of said vaginal incision and non-traumatizingly guiding said needle along the symphysis pubis to a second point about 3 cm to the left of a median line at the superior border of the symphysis pubis and passing said needle through the skin at this second point;

(14) incising the skin with a cutaneous incision about 0.5 cm in length at said second point;

(15) removing said trocar from said needle while leaving the cannula in place

(16) introducing the first end of said thread from the other of said pair of implants into said cannula until it protrudes into the vagina;

(17) withdrawing said cannula through the vagina;

(18) introducing said needle at the left distal extremity of said vaginal incision and non-traumatizingly guiding said needle along the symphysis pubis to said incision of step (14);

(19) removing said trocar from said needle while leaving the canula in place;

(20) introducing the second end of said thread from the other of said pair of implants into said cannula until it protrudes into the vagina;

(21) withdrawing said cannula through the vagina;

(22) burying each of said implants under the skin over the symphysis pubis;

(23) adjusting the urethro-vesical angle to a desired position;

(24) tying the ends of said threads from the right side to respective ends of said threads from the left side to hold the desired urethro-vesical angle.

Additionally, the present invention provides a kit for use in the surgical correction of female urinary stress incontinence comprising:

at least one needle, said needle comprising a cannula and a trocar, said cannula being receivable of said trocar, said trocar being removably disposable within said cannula, said needle being bendable to a desired degree of curvature; and a pair of implants, each of said implants comprising a head portion and a suture portion, said head portion adapted to rest on the pubic bone, said suture portion comprising a surgical suture acceptable, substantially non-biodegradable thread connected to said head portion; said thread having a first end and a second end disposed on a single side of said head portion, said first and second ends being guidingly receivable within s id cannula.

In a particularly preferred embodiment, the kit comprises:

a pair of implants, each of said implants comprising a head portion and a suture portion, said head portion comprising a substantially figure eight shaped member having a central cross bar, said suture portion comprising a surgical suture acceptable, substantially non-biodegradable thread having a first end, a second end and a central portion, said central portion being wrapped about said central cross bar with said first and second ends disposed on a single side of said figure eight shaped member;

a pair of needles, each of said needles comprising a cannula and a trocar, said cannula being receivable of said trocar, said trocar being removably disposable within said cannula, each of said needles being bendable to a desired degree of curvature, said cannula, in use, being guidingly receivable of said first end and said second end of said thread;

a tray for supporting and packaging said pair of needles and said pair of implants.

The present invention also provides a saddle for supporting a neck portion of the female urethra comprising:

a substantially rectangular, planar base, said base having an upper surface, a lower surface and four corners;

a pair of arms protruding upwardly and outwardly from a central portion of said upper surface of said base, said arms being integrally formed with said base and forming a substantially V-shaped notch therewith;

a reinforcing element attached to said lower surface of said base and substantially coextensive therewith;

means defining an aperture in each of the four corners of said base, each said aperture passing through said base and said reinforcing element.

BRIEF DESCRIPTION OF THE DRAWING FIGURES

FIG. 1A is a front view of a surgical implant, according to the present invention, useful in the surgical procedure of the present invention.

FIG. 1B is a side view of the surgical implant illustrated in FIG. 1A.

FIG. 1C is a top view of the surgical implant illustrated in FIG. 1A.

FIGS. 5A-5G illustrates the surgical procedure of the present invention.

DETAILED DESCRIPTION OF THE INVENTION

Figure 2:
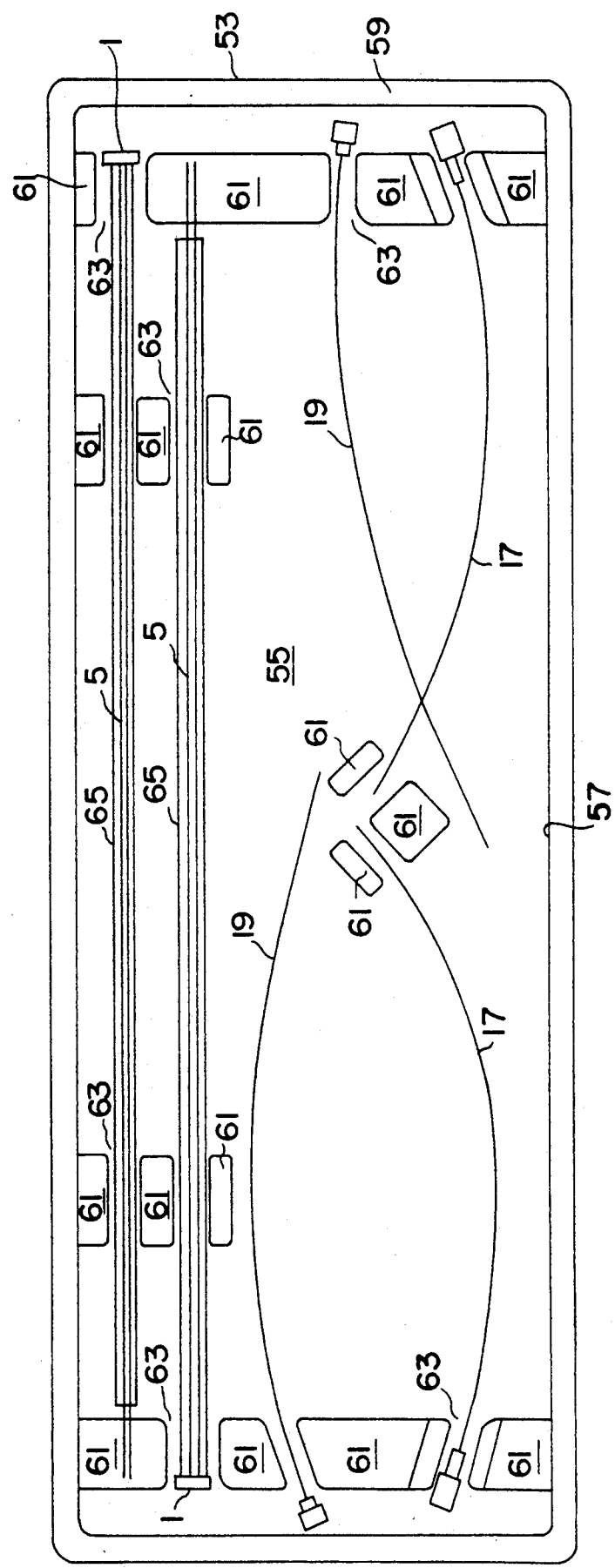
FIG. 2 is a plan view of a kit according to the present invention.

The present invention provides a surgical corrective technique for all human female stress urinary incontinence including fibrous perineal tissue due to irradiation by surgery or trauma. In particular, the technique is particularly suitable for patients suffering from coronary artery disability and chronic obstructive pulmonary illness, as well as elderly patients and patients suffering from Alzheimer's disease, etc. The only contra-indication is for patients whose vaginal tissue cannot support abdominal pressure. Bladder atony, in itself, is a contra-indication.

A proper diagnosis depends upon a pertinent questionnaire stipulating the frequency and the quantity of urinary incontinence. Conscientious study of the matter concerning bladder instability is also required.

A proper diagnosis also depends upon an adequate physical examination. In particular, after a complete micturition in the lithotomy position, the examination must reveal the degree of cysto-urethrocele as well as the mobility of the perineal and urethral tissue structures. Then, a cystoscope is introduced into the urethra, and residual urine is recorded and the bladder is then slowly distended, without pressure, while the urethra and bladder are visually inspected. The length of the urethra is recorded at the start of the inspection and when the bladder is full, but not distended. The cystoscope is removed and the patient is asked to cough several times. Stress incontinence is clearly noted when urine exits the urethral meatus simultaneously with the coughing. A delay of a few seconds in the incontinence indicates a hyporeflexic or unstable bladder. Finally, the Bonney Test (Marshall) is performed to confirm the continence and to indicate the necessary degree of urethropexy.

Upon a diagnosis dictating surgical intervention, the following technique is utilized.

Preparation

A urine culture is taken and, if the urine culture is negative, no antibiotics are necessary. A pre-operative medication, e.g., Diazepam (5 gm) is administered to alleviate anxiety, with the patient in the lithotomy position, knees slightly withdrawn.

Local Anesthesia

A catheter, e.g., a No. 18 Foley catheter, is placed to empty the bladder. Then, a local anesthetic, e.g., 4 cc of Xylocaine 2%, is injected about 3 cm to the left and about 3 cm to the right of the median line, precisely at the superior border of the symphysis pubis up to about 4-5 cm in depth. Afterwards, a small retractor allows visualization of the urethro-vesical junction region in the vagina, and a local anesthetic, e.g., about 2 cc of Xylocaine 2%, is injected at this point.

Intervention

As will become apparent hereinafter, the intervention comprises the placement of two implants which will anchor sutures holding the urethro-vesical juncture at a desired angle.

One of these implants is illustrated in Figs. 1A, 1B, and 1C. As may be readily ascertained, the implant, generally indicated at 1, comprises a head portion 3 and a suture portion 5. The head portion 3 is adapted to rest on the pubic bone (symphysis pubis) and is preferably of a substantially figure eight configuration having a central cross bar 7, when viewed from above. The head portion 3 may be formed of any medically acceptable non-biodegradable implant material, preferably a metallic material such as the surgical titanium alloy having the composition given in Table 1.

TABLE 1

| Component | % by wt. |
|---|---|
| Nitrogen | 0.05 |
| Carbon | 0.08 |
| Hydrogen | 0.012 Maximum |
| Iron | 0.025 |
| Oxygen | 0.13 |
| Aluminum | 5.5-6.5 |

TABLE 1-continued

| Component | % by wt. |
| --- | --- |
| Vanadium | 3.5–4.5 |
| Titanium | Balance |

Such a titanium alloy has a tensile strength of about 130,000 psi and an elongation of about 120,000 psi. If desired, the head portion 3 may be encased in a layer of a biologically acceptable coating material 9 (shown in phantom lines), e.g., medical grade silicone rubber.

The suture portion 5 comprises a surgical suture acceptable, substantially non-biodegradable thread having a first end 11, a second end 13 and a central portion 15. The central portion 15 is wrapped about the central cross bar 7 with the first end 11 and the second end 13 disposed on the same side of the head portion 3. The thread used for the suture portion may be any conventionally available, non-biodegradable suture material, e.g., 0.5 mm diameter Surgilen (Blue) or Prolene. Typically, the first end 11 and the second end 13 will extend 25–40 cms, preferably 30–35 cms, from the head portion 3.

The head portion 3, typically, has a length (A) of about 10–15 mm, preferably, about 12 mm; a width (C) of about 4–5 mm; and a height (B) of about 3–4 mm.

Figure 4:
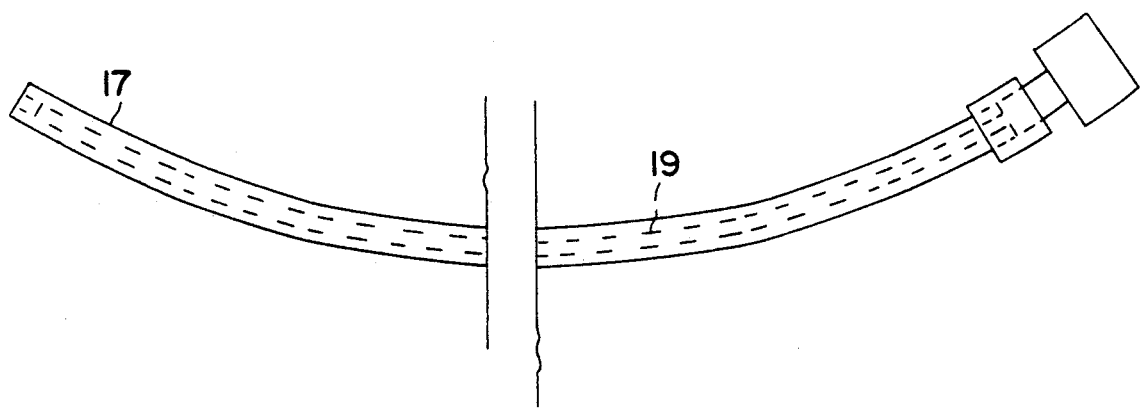
FIG. 4 illustrates a bendable needle comprising a cannula and a trocar as utilized in the present invention.

The intervention generally requires the utilization of at least one needle, preferably a pair of needles. The needles, as illustrated in FIGS. 2 and 4, each comprise a cannula 17 and a trocar 19. The trocar is removably, slidingly, disposable with the cannula. Each of the needles is bendable to a desired degree of curvature. The needles are generally supplied with a radius of curvature of about 100–105 mm, preferably about 102 mm, but may be bent to conform to the internal curve of the patients vagina. The needles are generally about 150 mm long with the cannula having an outside diameter of about 0.80 to 0.95 mm and with the trocar having an outside diameter of about 0.60 mm, e.g., a 19.5 gauge needle.

Figure 5B:
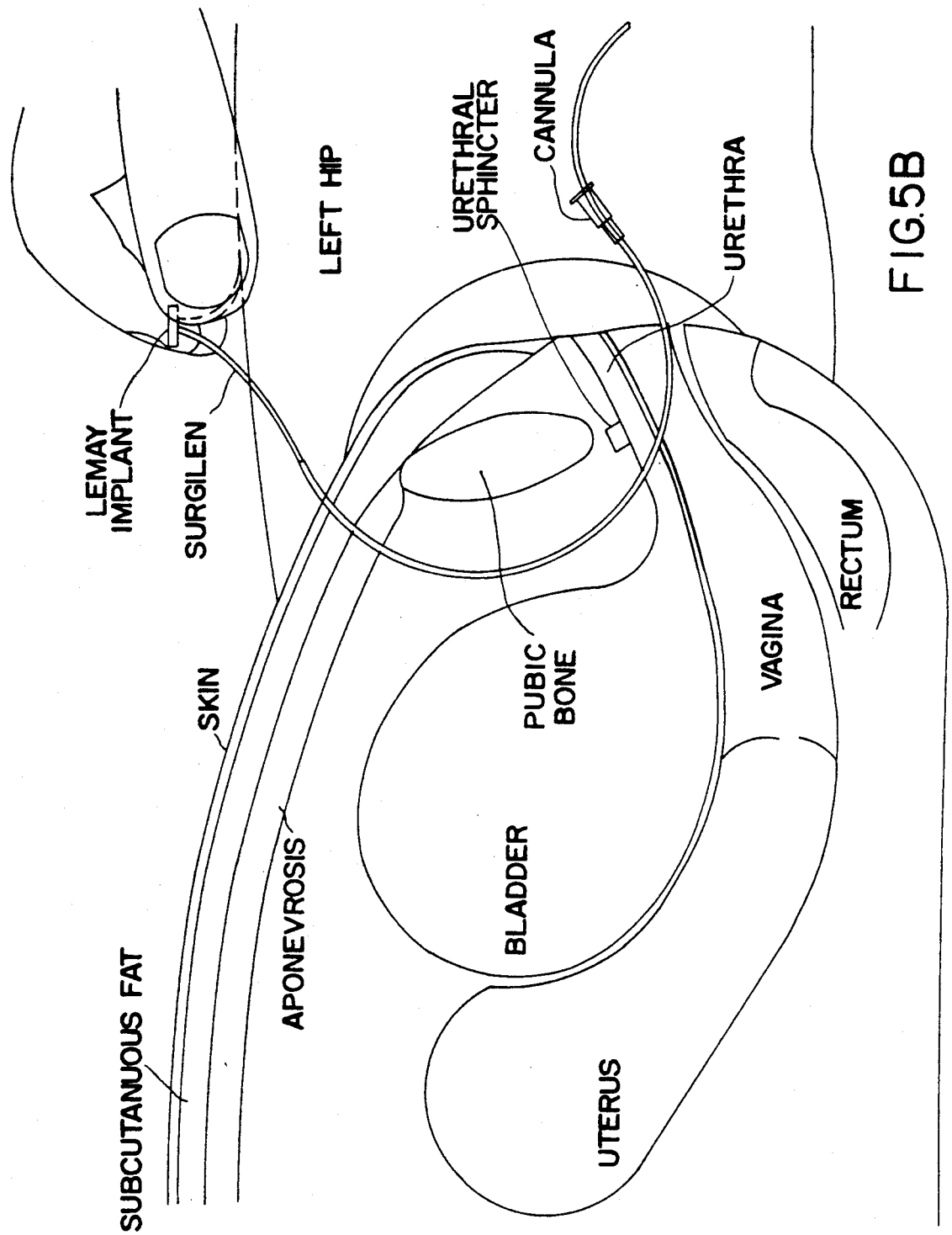
Figure 5E:
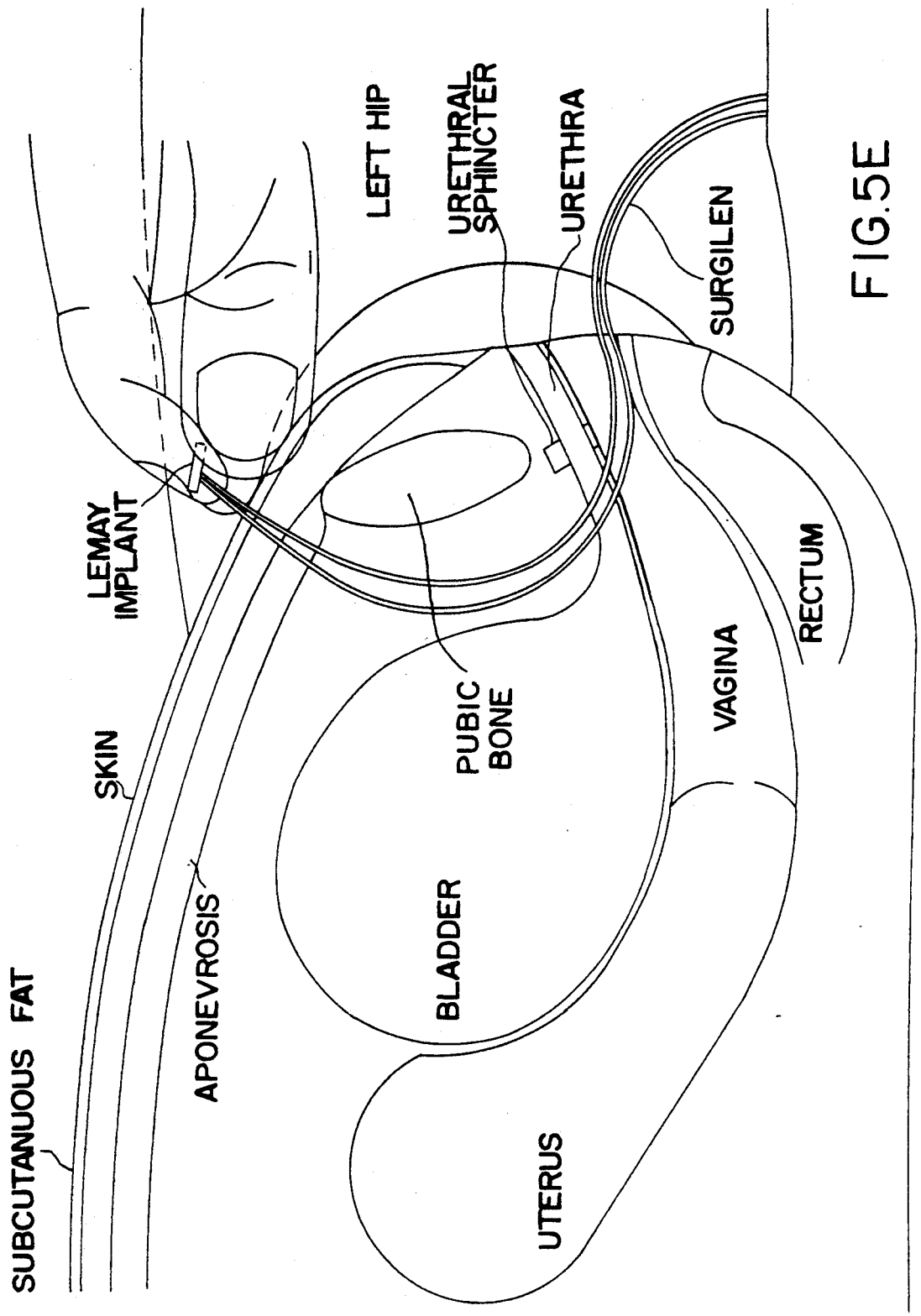
Figure 5G:
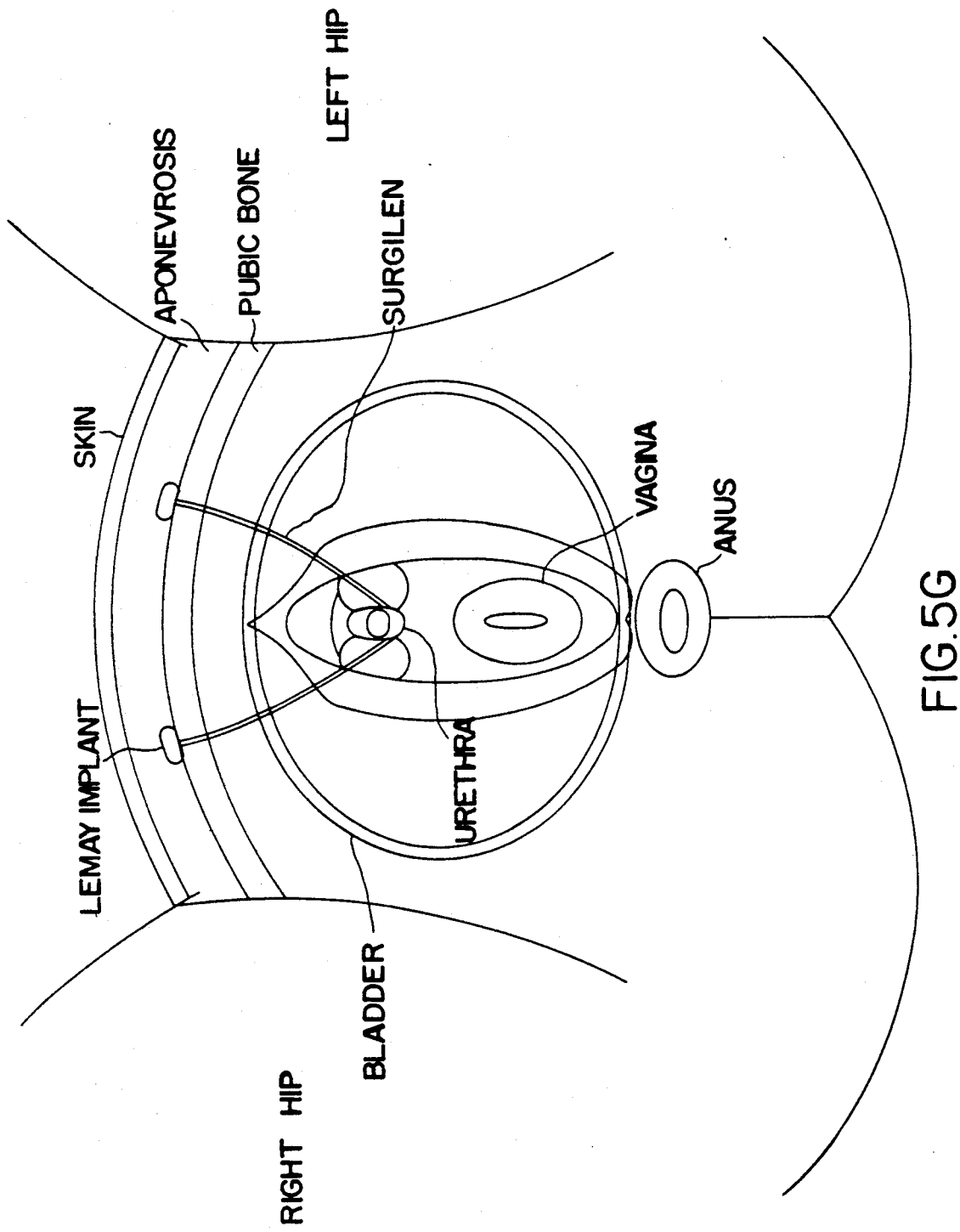

The intervention generally proceeds, as follows:

(1) incising only the vaginal mucosa with an incision about 1 cm in length at the urethro-vesical junction;

(2) introducing said needle at the right distal extremity of said vaginal incision and non-traumatizingly guiding said needle along the symphysis pubis to a first point about 3 cm to the right of a median line at the superior border of the symphysis pubis and passing said needle through the skin at this first point (FIG. 5A);

(3) incising the skin with a cutaneous incision about 0.5 cm in length at said first point;

(4) removing said trocar from said needle while leaving the cannula in place;

(5) introducing the first end of said thread from one of said pair of implants into said cannula until it protrudes into the vagina (FIG. 5B);

(6) withdrawing said cannula through the vagina;

(7) introducing said needle at the right distal extremity of said vaginal incision and non-traumatizingly guiding said needle along the symphysis pubis to said incision of step (5) FIG. 5C;

(8) removing said trocar from said needle while leaving the cannula in place;

(9) introducing the second end of said thread from said one of said pair of implants into said cannula until it protrudes into the vagina (FIG. 5D);

(10) withdrawing said cannula through the vagina (FIG. 5E);

(11) introducing said needle at the left distal extremity of said vaginal incision and non-traumatizingly guiding said needle along the symphysis pubis to a second point about 3 cm to the left of a median line at the superior border of the symphysis pubis and passing said needle through the skin at this second point (as similarly illustrated in FIG. 5A);

(12) incising the skin with a cutaneous incision about 0.5 cm in length at said second point;

(13) removing said trocar from said needle while leaving the cannula in place;

(14) introducing the first end of said thread from the other of said pair of implants into said cannula until it protrudes into the vagina (as similarly illustrated in FIG. 5B);

(15) withdrawing said cannula through the vagina;

(16) introducing said needle at the left distal extremity of said vaginal incision and non-traumatizingly guiding said needle along the symphysis pubis to said incision of step (14) (as similarly illustrated in FIG. 5C);

(17) removing said trocar from said needle while leaving the canula in place;

(18) introducing the second end of said thread from the other of said pair of implants into said cannula until it protrudes into the vagina (as similarly illustrated in FIG. 5D);

(19) withdrawing said cannula through the vagina (as similarly illustrated in FIG. 5E);

(20) burying each of said implants under the skin over the symphysis pubis (FIG. 5F);

(21) adjusting the urethro-vesical angle to a desired position;

(22) tying the ends of said threads from the right side to respective ends of said threads from the left side to hold the desired urethro-vesical angle (FIG. 5G).

If desired, the ends of the respective threads may be threaded through a reinforcing element to provide additional support. Such a reinforcement may be as simple as a small strip of biologically acceptable cloth, e.g., medical grade Dacron (polyethylene terephthalate polyester).

Figure 3B:
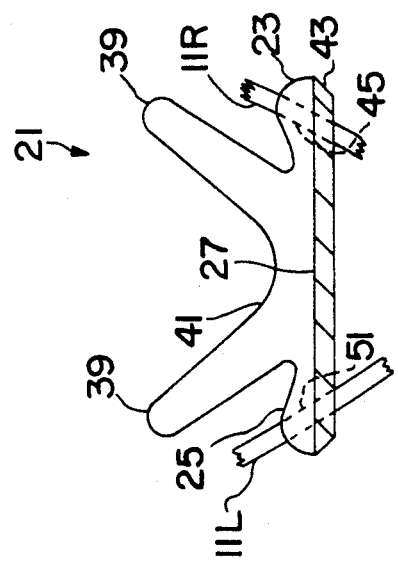
FIG. 3B is a side view of the saddle illustrated in FIG. 3A.
Figure 3C:
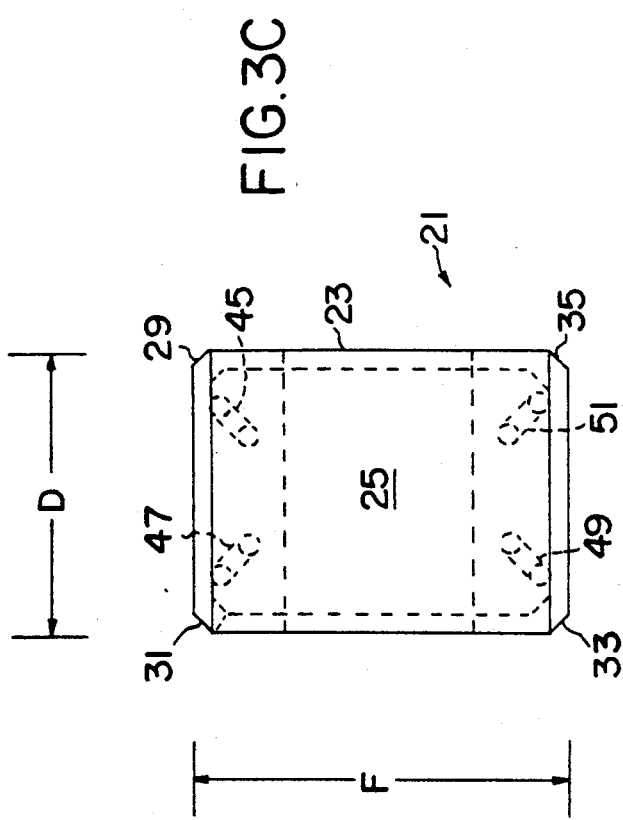
FIG. 3C is a top view of the saddle illustrated in FIG. 3A.
Figure 3A:
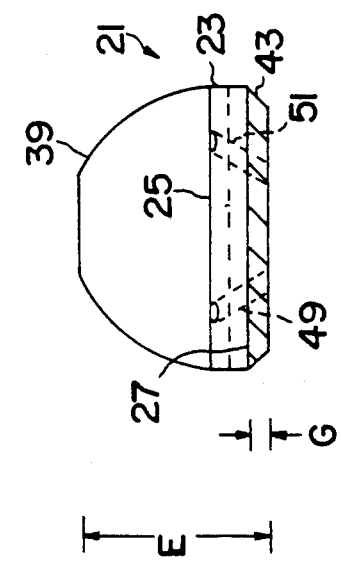
FIG. 3A is a front view of a saddle, according to the present invention, useful in the surgical procedure of the present invention.

However, in the case of a reoccurrence of incontinence after a first procedure, as noted above, a saddle as illustrated in FIGS. 3A, 3B and 3C may be used to hold the neck of the urethra, following its contour, while providing increased rigidity. The saddle, generally indicated at 21, comprises a substantially rectangular, planar base 23 having an upper surface 25, a lower surface 27 and four corners. A pair of arms 37, 39 protrude upwardly and outwardly from a central portion 41 of the upper surface 25 of the base 23. The arms are integrally formed with the base, from medical grade silicone rubber, and form a substantially V-shaped notch (best seen in FIG. 3B) to support the neck portion of the urethra proximate the urethro-vesical junction. A reinforcing element 43 is attached to the lower surface 27 of the base 23 and extends coextensively with the base 23. A series of bores 45, 47, 49, 51, having a diameter of about 0.7 mm, are provided in respective corners 29, 31, 33, 35 of the saddle 21 so as to receive the various ends of the threads 11L, 11R from the implants therethrough. The ends of the threads may be tied together to support the saddle, which in turn supports the neck portion of the urethra at a desired angle. The reinforcing element 43, which may be formed of medical grade polyester, e.g., Dacron (polyethylene terephthalate), prevents the threads from cutting the silicone rubber forming the base 23. The saddle 21, typically, has a length (D) of about 15 mm, although it may be supplied in different lengths so as to better conform to normally expected physiological differences between patients, e.g., lengths of 18.5 mm and 22 mm could also be supplied; a width (F) of about 20 mm; and a height (E) of about 10 mm. The reinforcing element 43 has a height (G) of about 1 mm.

Verification

Prior to the above-noted steps (20), (21) and (22), the Foley catheter is removed and a cystoscope is introduced to ensure that suture material is not present in the bladder, and, if necessary, to ensure that the bladder neck is not closed by traction on the implants. The bladder is left full and the instrument removed. Then, as noted above in the Intervention section, the implants may be buried under the skin, using hemostatic forceps, over the symphysis pubis while making sure not to create an umbilicus. By asking the patient to cough, to demonstrate incontinence, the sutures are then tied by lifting the urethro-vesical junction to a desired angular position. Again, the patient is asked to cough and continence is immediately observed. The sutures, parallel to one another, are now tied up at the same position.

The patient is then asked to try and void. This is generally impossible. A cystostomy is then performed or a Foley catheter is introduced. This concludes the procedure.

Post-Operation

The patient can be mobile, drink and eat right after her operation. An analgesic may be needed for several hours post-operatively. Antibiotic therapy is not indicated unless the urine culture was positive. Normal voiding may start as early as the next morning, after the cystostomy is closed or the catheter 10 removed. In 85% of the cases the cystostomy is closed or the catheter removed on the third day (although in some cases it has been as long as 22 days). Patients are examined at 3 days, 2 months, 6 months and 1 year after the procedure.

As previously noted, the present invention also provides a kit, illustrated in FIG. 2 to aid in effectuation of the surgical procedure disclosed above. The kit provides a pair of needles comprising two cannula 17 and two trocars 19 and a pair of implants 1. The needles and implants are packaged on a tray 53 comprising a planar central portion 55 surrounded by an upstanding circumferential wall 57 and a lip 59 extending outwardly from the top of the wall 57. A plurality of raised portions 61 are formed on central portion 55 and define a plurality of gaps 63 therebetween. A pair of hollow cylinders 65 supportingly receive respective suture portions 5 of the pair of implants 1 therein. These hollow cylinders 65 and portions of said trocars 19 and cannulae 17 are engagingly received within the gaps 63 so as to hold the implants, trocars and cannulae in predetermined positions on the tray 53. The tray may be formed of any substantially rigid material capable of withstanding conventional sterilization techniques without failure, e.g., a thermoset resin. A cover (not shown), such as a clear film, may be bonded to the lip 59 of the tray, or preferaby the tray may be packaged in a wrapping, to allow sterilization of the tray and its contents.

The above-described surgical procedure has been tested on 145 patients. A break-down of the patients by prior history and age is given in Table 2. The overall results, by prior hisotry grouping, are set forth in Table 4. The results, by age grouping, are set forth in Table 5. The explanation of those patients experiencing recurring incontinence are set forth in Table 6. The complications noted in the procedure are set forth in Table 7.

TABLE 2

| GROUPS | | |
|---|---|---|
| Prior History | | |
| (A) | First Surgery | 74 women |
| (B) | Recurring Incontinence (1 to 3 prior surgical procedures) | 65 women |
| (C) | More than 3 prior surgical procedures | 6 women |
| According to Age | | |
| (1) | More than 75 years old | 12 patients |
| (2) | From 65 to 75 years old | 52 patients |
| (3) | From 30 to 65 years old | 72 patients |
| (4) | Below 30 years old | 9 patients |

TABLE 3

| | OVERALL RESULTS | | | |
|---|---|---|---|---|
| TOTAL PATIENTS | TOTAL CONTINENCE | PARTIAL CONTINENCE (COMFORTABLE) | SUCCESS | FAILURE |
| Follow-up 6 mths 145 | 91% (133) | 3% (5) | 95% (138) | 5% (7) |
| Follow-up 1 yr 92 | 89% (81) | 4% (4) | 93% (85) | 7% (7) |

TABLE 4

| | | RESULTS BY PRIOR HISTORY | | |
|---|---|---|---|---|
| PATIENTS | TOTAL CONTINENCE | PARTIAL CONTINENCE (COMFORTABLE) | SUCCESS | FAILURE |
| GROUP A: 1ST SURGICAL PROCEDURE | | | | |
| 6 mths 74 | 90% (70/74) | 2% (2/74) | 97% (72/74) | 2% (2/74) |
| 1 yr 48 | 90% (43/48) | 6% (3/48) | 96% (46/48) | 4% (2/48) |
| GROUP B: FROM 1 TO 3 PRIOR SURGICAL PROCEDURES | | | | |
| 6 mths 65 | 90% (59/65) | 3% (2/63) | 93% (61/65) | 6% (4/65) |
| 1 yr 38 | 90% (34/38) | 2% (1/38) | 96% (35/38) | 7.5% (3/38) |
| GROUP C: MORE THAN 3 PRIOR SURGICAL PROCEDURES | | | | |
| 6 mths 6 | 66% (4/6) | 0% | 66% (4/6) | 33% (2/6) |
| 1 yr 6 | 66% (4/6) | 0% | 66% (4/6) | 33% (2/6) |

TABLE 5

| | | TOTAL CONTINENCE | PARTIAL CONTINENCE (COMFORTABLE) | SUCCESS | FAILURE |
|---|---|---|---|---|---|
| >75 years | 6 mths | 12 83% 10/12 | 0% 0/12 | 83% 10/12 | 17% 2/12 |
| | 1 yr | 7 71% 5/7 | 15% 1/7 | 85% 6/7 | 15% 1/7 |
| From 65 to 75 | 6 mths | 52 94% 49/52 | 2% 1/52 | 96% 50/52 | 4% 2/52 |
| | 1 yr | 33 91% 30/33 | 3% 1/33 | 94% 31/33 | 6% 2/33 |
| From 30 to 65 | 6 mths | 72 93% 67/72 | 4% 3/72 | 97% 70/72 | 3% 2/72 |
| | 1 yr | 45 88% 40/45 | 6% 3/45 | 94% 43/45 | 4% 2/45 |
| <30 years | 6 mths | 9 77% 7/9 | 11% 1/9 | 88% 8/9 | 11% 1/9 |
| | 1 yr | 7 70% 5/7 | 15% 1/7 | 85% 6/7 | 15% 1/7 |

TABLE 6

RECURRING INCONTINENCE 7 patients showed recurring incontinence:

Two (2) patients had a neurogenic bladder and 1 of those two (2) was re-operated without success.
In two (2) patients the surgery was considered incomplete and we simply placed two implants in a more proximal location.
In three (3) patients the slings (sutures) migrated in the vagina; the implants were replaced and Dacron was inserted in the fundus of the vagina.

TABLE 7

COMPLICATIONS

Major:
A retroperitoneal hematoma (Factor VIII) drained 21 days later.
Minor:

| | |
|---|---|
| Infection, following implants | 6/290 |
| Expulsion of implants through skin | 2/290 |
| Excessive Pain (implant removed) | 1/145 |
| Intravesical slings "sutures" (prior to cystoscopy) | 3/290 |
| Inflammatory reaction >10 days | 6/145 |
| Pain | 2/145 |
| Urinary retention   more than 3 days | 21/145 |
| more than 6 days | 6/145 |

The above described transfixation technique is totally unique in that it uses implants on the symphysis pubis and in that it is performed under only local anesthesia, as compared to existing procedures. It requires only a short hospital stay and it is equally applicable to the young and athletically inclined person and the high-risk surgical patient. If necessary, it is also a repeatable technique.

What is claimed is:

1. A kit for use in the surgical correction of female urinary stress incontinence comprising:
   at least one needle, said needle comprising a cannula and a trocar, said cannula being receivable of said trocar, said trocar being removably disposable within said cannula, said needle being bendable to a desired degree of curvature; and
   a pair of implants, each of said implants comprising a head portion and a suture portion, said head portion adapted to rest on the pubic bone, said head protion comprising a substanitally figure eight shaped member of surgical titanium having a central cross bar and said sutrue portion comprising a surgical suture acceptable, substantially non-biodegradable thread having a first end, a second end and a central portion, said central portion being wrapped about said central cross bar with said first and second ends disposed on a single side of said head portion, said first and second ends being guidingly receivable within said cannula.

2. The kit according to claim 1, comprising a pair of said needles.

3. The kit according to claim 1, further comprising a tray for engagingly supporting and packaging said at least one needle and said pair of implants.

4. The kit according to claim 3, wherein said tray is sterilizable.

5. A kit for use in the surgical correction of female urinary stress incontinence comprising:
   a pair of implants, each of said implants comprising a head portion and a suture portion, said head portion comprising a substantially figure eight shaped member of surgical titanium having a central cross bar, said suture portion comprising a surgical suture acceptable, substantially non-biodegradable thread having a first end, a second end and a central portion, said central portion being wrapped about said central cross bar with said first and second ends disposed on a single side of said figure eight shaped member;
   a pair of needles, each of said needles comprising a cannula and a trocar, said cannula being receivable of said trocar, said trocar being removably disposable within said cannula, each of said needles being bendable to a desired degree of curvature, said cannula, in use, being guidingly receivable of said first end and said second end of said thread;
   a tray for supporting and packaging said pair of needles and said pair of implants.

6. The kit according to claim 5, wherein said tray includes holding means for holding said pair of needles and said pair of implants in predetermined positions on said tray.

7. The kit according to claim 6, wherein said holding means comprises a pair of hollow cylinder members supportingly receivable of respective suture portions of said pair of implants therein.

8. The kit according to claim 7, wherein said holding means further comprises a plurality of raised portions formed on said tray, said plurality of raised portions defining a plurality of gaps therebetween, at least a portion of said plurality of gaps being engagingly receivable of respective portions of said pair of hollow cylinder member and said pair of needles.

9. The kit according to claim 5, wherein said tray is sterilizable.

10. The kit according to claim 5, wherein each of said pair of needles is about 150 mm long.

11. The kit according to claim 10, wherein for each of said pair of needles, said cannula has an outside diameter of about 0.80 to 0.95 mm and said trocar has an outside diameter of about 0.60 mm, said trocar being slidable within said cannula.

12. The kit according to claim 10, wherein each of said pair of needles is provided with a predetermined curvature.

13. The kit according to claim 12, wherein said predetermined curvature has a radius of curvature of about 102 mm.

14. The kit according to claim 5, wherein said head portion is encased within a coating of medical grade polymer.

15. The kit according to claim 14, wherein said polymer is a silicone.

16. A saddle for supporting a neck portion of the female urethra comprising
- a substantially rectangular, planar abase, said base having an upper surface, a lower surface and four corners;
- a pair of arms protruding upwardly and outwardly from a central portion of said upper surface of said base, said arms being integrally formed with said base and forming a substantially V-shaped notch therewith;
- a reinforcing element attached to said lower surface of said base and substantially coextensive therewith;
- means defining an aperture in each of the four corners of said base, each said aperture passing through said base and said reinforcing element.

17. The saddle according to claim 16, wherein said reinforcing element is formed of medical grade polyester.

18. The saddle according to claim 17, wherein said polyester is polyethylene terephthalate.

19. The saddle according to claim 17, wherein said base is formed of medical grade silicone rubber.

20. A method for surgically correcting female urinary stress incontinence comprising the steps of
- (1) providing a pair of implants, each of said implants comprising a head portion and a suture portion, said head portion adapted to rest on the symphysis pubis, said suture portion comprising a surgical suture acceptable, substantially non-biodegradable thread connected to said head portion, said thread having a first end and a second end disposed on a single side of said head portion;
- (2) providing at least one needle, said at least one needle comprising a cannula and a trocar, said cannula being receivable of said trocar, said trocar being removably disposable within said cannula, said at least one needle being bendable to a desired degree of curvature, said first and second ends of said thread being guidingly receivable within said cannula;
- (3) incising only the vaginal mucosa with an incision about 1 cm in length at the urethro-vesical junction;
- (4) introducing said needle at the right distal extremity of said vaginal incision and non-traumatizingly guiding said needle along the symphysis pubis to a first point about 3 cm to the right of a median line at the superior border of the symphysis pubis and passing said needle through the skin at this first point;
- (5) incising the skin with a cutaneous incision about 0.5 cm in length at said first point;
- (6) removing said trocar from said needle while leaving the cannula in place;
- (7) introducing the first end of said thread from one of said pair of implants into said cannula until it protrudes into the vagina;
- (8) withdrawing said cannula through the vagina;
- (9) introducing said needle at the right distal extremity of said vaginal incision and non-traumatizingly guiding said needle along the symphysis pubis to said incision of step (5);
- (10) removing said trocar from said needle while leaving the cannula in place;
- (11) introducing the second end of said thread from said one of said pair of implants into said cannula until it protrudes into the vagina;
- (12) withdrawing said cannula through the vagina;
- (13) introducing said needle a the left distal extremity of said vaginal incision and non-traumatizingly guiding said needle along the symphysis pubis to a second point about 3 cm to the left of a median line at the superior border of the symphysis pubis and passing said needle through the skin at this second point;
- (14) incising the skin with a cutaneous incision about 0.5 cm in length at said second point;
- (15) removing said trocar from said needle while leaving the cannula in place;
- (16) introducing the first end of said thread from the other of said pair of implants into said cannula until it protrudes into the vagina;
- (17) withdrawing said cannula through the vagina;
- (18) introducing said needle at the left distal extremity of said vaginal incision and non-traumatizingly guiding said needle along the symphysis pubis to said incision of step (14);
- (19) removing said trocar from said needle while leaving the canula in place;
- (20) introducing the second end of said thread from the other of said pair of implants into said cannula until it protrudes into the vagina;
- (21) withdrawing said cannula through the vagina;
- (22) burying each of said implants under the skin over the symphysis pubis;
- (23) adjusting the urethro-vesical angle to a desired position;
- (24) tying the ends of said threads from the right side to respective ends of said threads from the left side to hold the desired urethro-vesical angle.

21. The method according to claim 20, wherein, prior to step (3), an anesthetically-effective amount of a local anesthetic is injected at the urethro-vesical junction; and anesthetically-effective amounts of a local anesthetic are injected at a point about 3 cm to the right of the median line at the superior border of the symphysis pubis to a depth of about 4–5 cm and at a point about 3 cm to the left of the median line at the superior border of the symphysis pubis to a depth of about 4–5 cm.

* * * * *